(12) United States Patent
Dicciani et al.

(10) Patent No.: US 11,766,222 B2
(45) Date of Patent: *Sep. 26, 2023

(54) ALGORITHM FOR BREATHING EFFICIENCY

(71) Applicant: RTM Vital Signs LLC, Philadelphia, PA (US)

(72) Inventors: Nance K. Dicciani, Lower Gwynedd, PA (US); Denise L. Devine, Media, PA (US); Magdalena K. Bosak, Collingswood, NJ (US)

(73) Assignee: RTM Vital Signs LLC, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/183,251

(22) Filed: Mar. 14, 2023

(65) Prior Publication Data
US 2023/0218239 A1    Jul. 13, 2023

Related U.S. Application Data

(63) Continuation of application No. 17/854,256, filed on Jun. 30, 2022, now Pat. No. 11,622,728.
(Continued)

(51) Int. Cl.
*A61B 5/00* (2006.01)
*A61B 5/087* (2006.01)
(Continued)

(52) U.S. Cl.
CPC ............ *A61B 5/7264* (2013.01); *A61B 5/087* (2013.01); *A61B 5/0816* (2013.01); *A61B 2562/0204* (2013.01); *A63B 2024/0065* (2013.01)

(58) Field of Classification Search
None
See application file for complete search history.

(56) References Cited

U.S. PATENT DOCUMENTS 5,010,890 A * 4/1991 Pfohl .................. A61B 5/0017
600/528
5,853,005 A * 12/1998 Scanlon ............... A61B 5/6896
381/166

(Continued)

OTHER PUBLICATIONS

Naranjo, J, et al. "A Nomogram for Assessment of Breathing Patterns during Treadmill Exercise." British Journal of Sports Medicine, vol. 39, No. 2, 2005, pp. 80-83., doi:10.1136/bjsm.2003.009316.

*Primary Examiner* — Michael R Bloch
(74) *Attorney, Agent, or Firm* — Christopher & Weisberg, P.A.

(57) ABSTRACT

A method of determining a fitness level of user with a physiological sensor. The method includes measuring a physiological value of the user with the physiological sensor, correlating the measured physiological value into a measurement of the user's respiratory rate and tidal volume, calculating a second respiratory rate value using the measured tidal volume, calculating a breathing efficiency (BE) ratio based on a comparison of the user's measured respiratory rate and the calculated second respiratory rate value, correlating the calculated BE ratio to a predetermined threshold, and assigning a classification to the user based on the calculated BE ratio. The classification is indicative of the user's respiratory function performance.

5 Claims, 7 Drawing Sheets

Related U.S. Application Data

(60) Provisional application No. 63/217,487, filed on Jul. 1, 2021.

(51) Int. Cl.
*A61B 5/08* (2006.01)
*A63B 24/00* (2006.01)

(56) References Cited

U.S. PATENT DOCUMENTS

| | | | |
|---|---|---|---|
| 11,000,191 B2 | 5/2021 | Joseph et al. | |
| 11,000,212 B2 | 5/2021 | Joseph et al. | |
| 2006/0047215 A1* | 3/2006 | Newman | A61B 5/282 600/528 |
| 2007/0118054 A1* | 5/2007 | Pinhas | G16H 40/67 600/587 |
| 2007/0167855 A1* | 7/2007 | Shin | A61B 5/7405 600/533 |
| 2011/0172552 A1* | 7/2011 | Rothman | A61B 5/6822 600/529 |
| 2015/0150503 A1* | 6/2015 | Pamnani | A61B 5/4878 600/438 |
| 2018/0256087 A1* | 9/2018 | Al-Ali | A61B 5/0816 |
| 2020/0397306 A1* | 12/2020 | Frank | G01J 5/10 |
| 2021/0104173 A1* | 4/2021 | Pauley | G16H 20/60 |
| 2021/0113099 A1* | 4/2021 | Rogers | A61B 5/4803 |
| 2021/0251520 A1 | 8/2021 | Joseph et al. | |
| 2021/0259557 A1* | 8/2021 | Frank | G01J 3/50 |

* cited by examiner

ALGORITHM FOR BREATHING EFFICIENCY

CROSS-REFERENCE TO RELATED APPLICATION

This application is a Continuation of U.S. application Ser. No. 17/854,256, filed Jun. 30, 2022 which claims priority and the benefit of U.S. Application Ser. No. 63/217,487, filed Jul. 1, 2021.

TECHNICAL FIELD

This disclosure relates to a method and system for a method of determining a respiratory fitness level of a user with diagnostic algorithms that quantify and analyze the pattern of the user's respiratory rate (RR), tidal volume (TV), and breathing efficiency (BE), among other physiological conditions.

BACKGROUND

Existing health, wellness, and fitness systems generally track physiological parameters such as heart rate, blood pressure, body temperature, etc. These physiological parameters may be tracked and relayed to a user via a smart device, such as a smart phone and/or a smart watch. Because smart watches are generally secured around a user's wrist or arm during exercise, they commonly include at least one sensor that is configured to be in contact with the user's skin to monitor the wearer's physiological parameters. However, because these smart watches and/or smart phones are not located proximate to the user's chest, throat, or mouth, they are unable to accurately monitor respiratory parameters such as respiratory rate and tidal volume of the user during exercise. Thus, this information is often not available to users following the completion of an exercise routine or physical activity.

Monitoring various respiratory values including breathing frequency, breathing effort, tidal volume and other related respiratory values can help monitor and interpret the health and well-being of an individual. Vital signs, such as respiration, are often overlooked, poorly documented, and undervalued in the clinical setting. Monitoring and interpreting various respiratory values can help to improve the understanding of respiratory physiology and clinical assessments. Respiratory rates can be an indicator of certain clinical deteriorations which often occur before other vital sign changes are detectable. This type of respiratory information can be used to improve the safety and outcomes of individuals based upon their respiratory values.

SUMMARY

The techniques of this disclosure generally relate to a method, device, and system for determining fitness levels.

In one aspect, a method of determining a fitness level of user with an acoustic measurement device configured to measure sound associated with airflow through a mammalian trachea. The acoustic measurement device is in communication with a controller having processing circuitry. The method includes correlating the measured sound into a measurement of the user's respiratory rate and tidal volume; calculating a second respiratory rate value using the measured tidal volume; calculating a breathing efficiency (BE) ratio based on a comparison of the user's measured respiratory rate and the calculated second respiratory rate value; correlating the calculated BE ratio to a predetermined threshold; and assigning a classification to the user based on the calculated BE ratio. The classification is indicative of the user's respiratory function performance.

In another aspect, the acoustic measurement device includes at least one sound transducer, the at least one sound transducer being configured to measure the sound associated with airflow through the mammalian trachea.

In another aspect, the assigned classification is one selected from the group consisting of an elite athlete level, a trained athlete level, and a lesser athlete level.

In another aspect, the elite athlete level classification is assigned when the BE ratio is greater than the predetermined threshold. The trained athlete level classification is assigned when the BE ratio is equal to the predetermined threshold. The lesser athlete level classification is assigned when the BE ratio is less than the predetermined threshold.

In another aspect, the elite athlete level has a BE>1.0, the trained athlete level has a BE=1.0, and the lesser athlete level has a BE<1.0.

In another aspect, the measurement of sound associated with airflow through the trachea occurs at least one from the group consisting of periodically, intermittently, and continuously.

In another aspect, the acoustic measurement device includes a housing, and the at least one sound transducer may be suspended within the housing.

In another aspect, the housing of the acoustic measurement device has a width between 0.5 cm and 3.5 cm.

In another aspect, the acoustic measurement device is in wireless communication with the controller.

In another aspect, the controller is a smart device.

In another aspect, the method further comprises filtering out a set of anomalous data and ambient noise from the measured sound vibrations.

In another aspect, the second respiratory rate value is calculated using the measured tidal volume with a first equation for men and a second equation for women, the first equation being $RR2 = 8.3465 e^{0.7458(tidal\ volume)}$ and the second equation being $RR2 = 9.6446 e^{0.9328(tidal\ volume)}$.

In one aspect, a method of determining a fitness level of a user with an acoustic measurement device at least one of before, during, or after physical activity. The acoustic measurement device includes a sound transducer configured to measure sound associated with airflow through a mammalian trachea. The method comprising correlating the measured sound into a measurement of the user's respiratory rate and tidal volume at a predetermined time interval; calculating a second respiratory rate value using the measured tidal volume; calculating a breathing efficiency (BE) ratio based on a comparison of the user's measured respiratory rate and the calculated second respiratory rate value; correlating the calculated BE ratio to a predetermined threshold; and assigning a classification to the user based on the calculated BE ratio. The classification may be one selected from the group consisting of: an elite athlete level, a trained athlete level, and a lesser athlete level.

In another aspect, the elite athlete level classification is assigned when the BE ratio is greater than the predetermined threshold, the trained athlete level classification is assigned when the BE ratio is equal to the predetermined threshold, and the lesser athlete level classification is assigned when the BE ratio is less than the predetermined threshold.

In another aspect, the measurement of sound associated with airflow through the trachea occurs at least one from the group consisting of periodically, intermittently, and continuously.

In another aspect, the acoustic measurement device includes a housing and a sound transducer, and wherein the sound transducer is suspended within the housing.

In another aspect, the housing of the acoustic measurement device has a width between 0.5 cm and 3.5 cm.

In another aspect, the acoustic measurement device is in communication with a controller configured, the controller being configured to correlate the measured sound into the measurement of the user's respiratory rate and tidal volume at a predetermined time interval, calculate the second respiratory rate value using the measured tidal volume, calculate the breathing efficiency (BE) ratio based on the comparison of the user's measured respiratory rate and the calculated second respiratory rate value, correlate the calculated BE ratio to the predetermined threshold, and assign the classification to the user based on the calculated BE ratio, the classification being one selected from the group consisting of the elite athlete level, the trained athlete level, and the lesser athlete level.

In another aspect, the controller is a smart device.

In another aspect, the method further comprises filtering out a set of anomalous data and ambient noise from the measured sound vibrations.

In another aspect, the method further comprises a housing, the housing is configured to releasably couple to skin of the mammalian trachea by an adhesive or an adjustable band.

In one aspect, a method of determining a fitness level of a user with an acoustic measurement device at least one of before, during, or after physical activity. The acoustic measurement device including a sound transducer configured to measure sound associated with airflow through a mammalian trachea the acoustic measuring device being in communication with a controller configured to perform the method. The method comprising correlating the measured sound into a measurement of the user's respiratory rate and tidal volume at a predetermined time interval; calculating a second respiratory rate value using the measured tidal volume; calculating a breathing efficiency (BE) ratio based on a comparison of the user's measured respiratory rate and the calculated second respiratory rate value for a predetermined point in time or over a predetermined period of time; correlating the calculated BE ratio to a predetermined threshold; and assigning a classification to the user based on the calculated BE ratio. The classification being one selected from the group consisting of an elite athlete level where this classification is assigned when the BE ratio is greater than the predetermined threshold, a trained athlete level where this classification is assigned when the BE ratio is equal to the predetermined threshold, and a lesser athlete level where this classification is assigned when the BE ratio is less than the predetermined threshold.

In one aspect, a method of determining a fitness level of a user includes providing a physiological sensor, measuring a physiological value of the user with the physiological sensor, correlating the measured physiological value into a measurement of the user's respiratory rate and tidal volume, calculating a second respiratory rate value using the measured tidal volume, calculating a breathing efficiency (BE) ratio based on a comparison of the user's measured respiratory rate and the calculated second respiratory rate value, correlating the calculated BE ratio to a predetermined threshold; and assigning a classification to the user based on the calculated BE ratio, the classification being indicative of the user's respiratory function performance.

In another aspect, the assigned classification is one selected from the group consisting of an elite athlete level, a trained athlete level, and a lesser athlete level.

In another aspect, the elite athlete level classification is assigned when the BE ratio is greater than the predetermined threshold, the trained athlete level classification is assigned when the BE ratio is equal to the predetermined threshold, and the lesser athlete level classification is assigned when the BE ratio is less than the predetermined threshold.

In another aspect, the elite athlete level has a BE>1.0, the trained athlete level has a BE=1.0, and the lesser athlete level has a BE<1.0.

In another aspect, the second respiratory rate value is calculated using the measured tidal volume with a first equation for men and a second equation for women, the first equation being $RR2=8.3465e^{0.7458(tidal\ volume)}$ and the second equation being $RR2=9.6446e^{0.9328(tidal\ volume)}$.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Before describing in detail exemplary embodiments, it is noted that the embodiments reside primarily in combinations of apparatus components and processing steps related to a method and system for determining a respiratory fitness level of a user with diagnostic algorithms that quantify and analyze the pattern of the user's respiratory rate (RR), tidal volume (TV), and breathing efficiency (BE), among other physiological conditions. The measurements including the RR, TV, BE, and other physiological measurements which are made using the method and systems may be continuously monitored, may be averaged over a period of time which may correspond to, for example, an exercise period, a physical/fitness performance evaluation period, or may be made for any other preset time interval. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

With reference to FIGS. 1-7, an acoustic measurement device such as, for example, a Tracheal Sound Sensor (TSS) 10, is depicted which is sized and configured to be releasably affixed to the skin of a mammal or user by an adhesive or adjustable elastic band. As described herein, in one embodiment the TSS 10 of the present invention may be configured similarly to the acoustic measurement device as set forth in U.S. Pat. No. 11,000,191, issued on May 11, 2021, and entitled "ACOUSTIC SENSOR AND VENTILATION MONITORING SYSTEM," which is incorporated herein by reference. The TSS 10 includes a housing 12 defining an at least partially enclosed chamber 14 therein. In one configuration, the housing 12 defines a width and a length of approximately 3.5 cm or less. For example, the housing 12 may be substantially cube shaped having a width of 3.5 cm or less, such as between 0.5 cm to 3.5 cm, a sphere or disc having a diameter of 3.5 cm or less, or another shape suitable for affixing to the user, including but not limited to an oval, a rectangle, or any other configuration.

The housing 12 may be composed of one or more materials, such as a lightweight plastic, metal, ceramic, or composite having integrated or added sound insulation material 16 on an exterior thereof, lining the interior of the chamber, or both, to attenuate ambient sound. Additionally, other active and passive noise cancellation techniques may be used as well, including additional sound transducers. For example, additional microphones and/or acoustic sensors may be added to the TSS 10 to provide active noise cancellation. Additionally and/or alternatively, sound insulation materials may be added to the TSS 10 to provide passive noise cancellation. Software may also be included in the TSS 10 to actively remove any noise from the respiratory data as well. The walls of the housing and lining may be separated by an air-filled space designed to attenuate ambient sound. The housing 12 may be manufactured from materials and structure that attenuates transmission of ambient sound into the chamber 14. In one configuration, an airtight seal is formed between the housing 12 and skin surface to isolate the inside of the TSS 10 from the external environment. In an alternative configuration, the housing 12 may be porous or have an external opening such that sound may penetrate the housing 12 from an ambient environment, depending on the application. In one configuration, the housing 12 defines a single opening 18 to provide access to the chamber 14, however, the number and size of the openings 18 are not limited to a particular number and size. The sound insulation material 16 may surround the housing 12 in all areas with the exception of around the opening 18. The housing 12 may define a dome shape, a bell shape, or any shape such that the chamber 14 is isolated from external sounds and optimized to measure the sounds of air movement within the trachea.

One or more sound transducers 20 may be affixed, either permanently or removably, within the chamber 14 of the housing 12 for measuring at least one of a respiratory rate and a tidal volume of the patient. The sound transducer 20 may be one or more microphones, for example, in the 20-2000 Hz range, configured to measure sound energy within the chamber 14 and transduce an acoustic signal into a digital signal. The miniature electronic microphones (electric, piezoelectric, or MEMS) transduce the mechanical vibrations caused by airflow within the proximal trachea during inhalation and exhalation with a high signal-to-noise ratio. In one configuration, the sound transducer 20 is located at an end of the housing 12 opposite an end of the housing 12 defining the opening 18 and may be suspended within the chamber 14 using, for example, an elongate rod or other suspension element (not shown) extending from the interior surface of the chamber 14 such that the sound transducer 20 is not in contact with the interior walls of the housing 12.

A flexible diaphragm 22 may be disposed within the opening 18 that is coextensive or slightly recessed within a surface of the housing 12. The diaphragm 22 may be a thin flexible material that resonates in response to sound energy, for example airflow through the trachea of a mammal, in a manner similar to a pediatric stethoscope head. In one configuration, the diaphragm 22 is electrically coupled to the sound transducer 20 such that when the diaphragm 22 resonates, the sound vibration is directly measured by the sound transducer 20. In other configurations, rather than being coupled to the diaphragm 22, the sound transducer 20 is in close proximity to the diaphragm 22, for example, immediately adjacent thereto to minimize any ambient sound measured by the sound transducer 20. In other configurations, the diaphragm 22 is the actual diaphragm of the sound transducer 20 and is directly coupled to an electromagnetic coil, capacitor, or piezoelectric crystal of the sound transducer 20. In one configuration, the interior of the housing 12 may define a curved semi-circle, dome, or other shape to focus the sound energy transduced from the diaphragm 22 on the skin surface directly into the sound transducer 20. For example, the sound transducer 20 and diaphragm 22 may be angled and positioned in a manner to measure sounds of the airflow as it enters and exits the larynx. In other configurations, the sound transducer 20 and the diaphragm 22 are aimed toward the airflow through the trachea. In one configuration, the sound transducer 20 is a piezoelectric film with adhesive that adheres to the skin surface adjacent or proximal to the trachea.

Continuing to refer to FIGS. 1-6, a wireless transmitter 24 may be coupled to the housing 12, which is in communication with the sound transducer 20. The wireless transmitter 24, which may transmit and receive, is configured to transmit the transduced acoustic signal measured by the sound transducer 20. In one configuration, the wireless transmitter 24 is included as part of a processing circuitry having one or more processors included within the housing 12. For example, the wireless transmitter 24 may transmit the measurement of the respiratory rate, the tidal volume, the heart rate, or other vital sign data, to a controller 26 which forms an acoustic ventilation monitoring system (AVMS) 27 in combination with the TSS 10. In one embodiment, the controller 26 may be a remote controller in the form of a smartphone, tablet, smartwatch, Echo™ device, Alexa™ device, cable box, or other mobile communication device or smart device configured to be held, coupled to, or in proximity to the patient, that communicates with the TSS 10 by Bluetooth® low-energy (BLE) or WiFi®, or another electronic handshake such that acoustic information may be relayed to the controller 26 for real-time processing. In another embodiment, the controller 26 may be sized and configured to be embedded within the housing 12 of the TSS 10. The controller 26 may further include processing circuitry 25 with one or more processors to process the data received from the TSS 10. In one or more embodiments, the processing circuitry 25 may include a processor 29 and a memory 31. In particular, in addition to or instead of a processor, such as a central processing unit, and memory, the processing circuitry 25 may comprise integrated circuitry for processing and/or control, e.g., one or more processors and/or processor cores and/or FPGAs (Field Programmable Gate Array) and/or ASICs (Application Specific Integrated Circuitry) adapted to execute instructions. The processor 29 may be configured to access (e.g., write to and/or read from) the memory 31 which may comprise any kind of volatile and/or nonvolatile memory, e.g., cache and/or buffer memory and/or RAM (Random Access Memory) and/or ROM (Read-Only Memory) and/or optical memory and/or EPROM (Erasable Programmable Read-Only Memory). The processing circuitry 25 may be configured to control any of the methods and/or processes described herein and/or to cause such methods, and/or processes to be performed, e.g., by the controller 26. Processor 29 corresponds to one or more processors 29 for performing functions described herein. The memory 31 is configured to store data, programmatic software code and/or other information described herein. In some embodiments, the software may include instructions that, when executed by the processor 29 and/or processing circuitry 25 causes the processor 29 and/or processing circuitry 25 to perform the processes described herein with respect to remote controller 26. For example, processing circuitry 25 of the remote controller 26 may include a control unit 33 that is configured to perform one or more functions described herein.

The results of such processing may be displayed on the display of the controller 26 or transmitted by the controller 26 to a remote location for further processing and/or analysis. As described herein, the AVMS 27 of the present invention is also capable of performing the operations as set forth in U.S. application Ser. No. 17/308,084, filed on May 5, 2021, and entitled "ACOUSTIC SENSOR AND VENTILATION MONITORING SYSTEM," and U.S. Pat. No. 11,000,212, issued on May 11, 2021, and entitled "ACOUSTIC SENSOR AND VENTILATION MONITORING SYSTEM," which are incorporated herein by reference.

The wireless transmitter 24 and the sound transducer 20 may be powered by a same rechargeable power source 28 such as, for example, a rechargeable battery. Although the power source 28 is shown in FIGS. 1-6 as being smaller size wise relative to some other components of TSS 10 disclosed herein, it is noted that the illustrated size of the power source 28 is merely exemplary and may be any shape or size. In one embodiment (not shown), the TSS 10 may be recharged within a dedicated housing unit that includes a rechargeable power source. When in the dedicated housing unit, the TSS 10 may be in electrical communication with the rechargeable power source such that TSS 10 may be rechargeable using inductive coupling or wired connection via a cable to a Universal Serial Bus (USB) port. A battery of the TSS 10 that lasts up to five or more days may be disposable. However, the battery of the TSS 10 may last for a longer and/or a shorter period of time as well.

As shown in FIGS. 1-5, the TSS 10 may include an adjustable elastic band or adhesive 30 adhered to the patient's skin proximate one of the tracheal notch or a lateral neck region of the patient to measure sound and/or vibrations associated with the patient's breathing. The adhesive 30 may also at least partially surround the opening 18. The adhesive 30 may be a double-sided tape or pad or other removable adhesive which allows the TSS 10 to be releasably adhered to the skin of the patient after remaining affixed to the patient for a predetermined period of time, for example, 1 hour-14 days. In one configuration, the adhesive 30 surrounds the opening 18 on the surface of the housing 12 without occluding or otherwise blocking the opening 18 to avoid interfering with sound waves entering the chamber 14. When in contact with the skin surface, the adhesive 30 provides an airtight seal for enhanced passive noise suppression from ambient sounds. The TSS 10 may further include an accelerometer 32, a temperature sensor 34, and/or a reflectance pulse oximeter 36, which may be positioned within the housing 12 and coupled to the power source 28 in communication with the controller 26. The 3-axis accelerometer 32 may be configured to measure a relative x-y-z position and a movement of the patient, such as the amount and pattern of head bobbing, body movement, body coordination, and body position in real-time to further estimate, in the case of, for example, a drug overdose, the degree of sedation and the trends of sedation over time. The accelerometer 32 also senses chest wall movement to monitor the onset/timing of inhalation and exhalation. The temperature sensor 34 may be integrated within the housing and used to detect a decrease or increase in body temperature. The reflectance pulse oximeter 36 may be configured to monitor percent hemoglobin oxygen saturation and the photoplethysmograph waveform, whether continuously, intermittently, or when the algorithm detects/predicts the onset of hypoventilation or a change in health. The pulse oximeter's waveform can be analyzed in real-time to estimate heart rate, heart rate variability, stroke volume, stroke volume variability, pre-load, myocardial contractility, systemic vascular resistance, cardiac output, and systemic blood pressure. In one configuration, at least a portion of the housing 12 may define a perimeter that is adjacent to and in contact with the temperature sensor 34, the accelerometer 32, the at least one sound transducer 20, and the adhesive 30.

Figure 1:
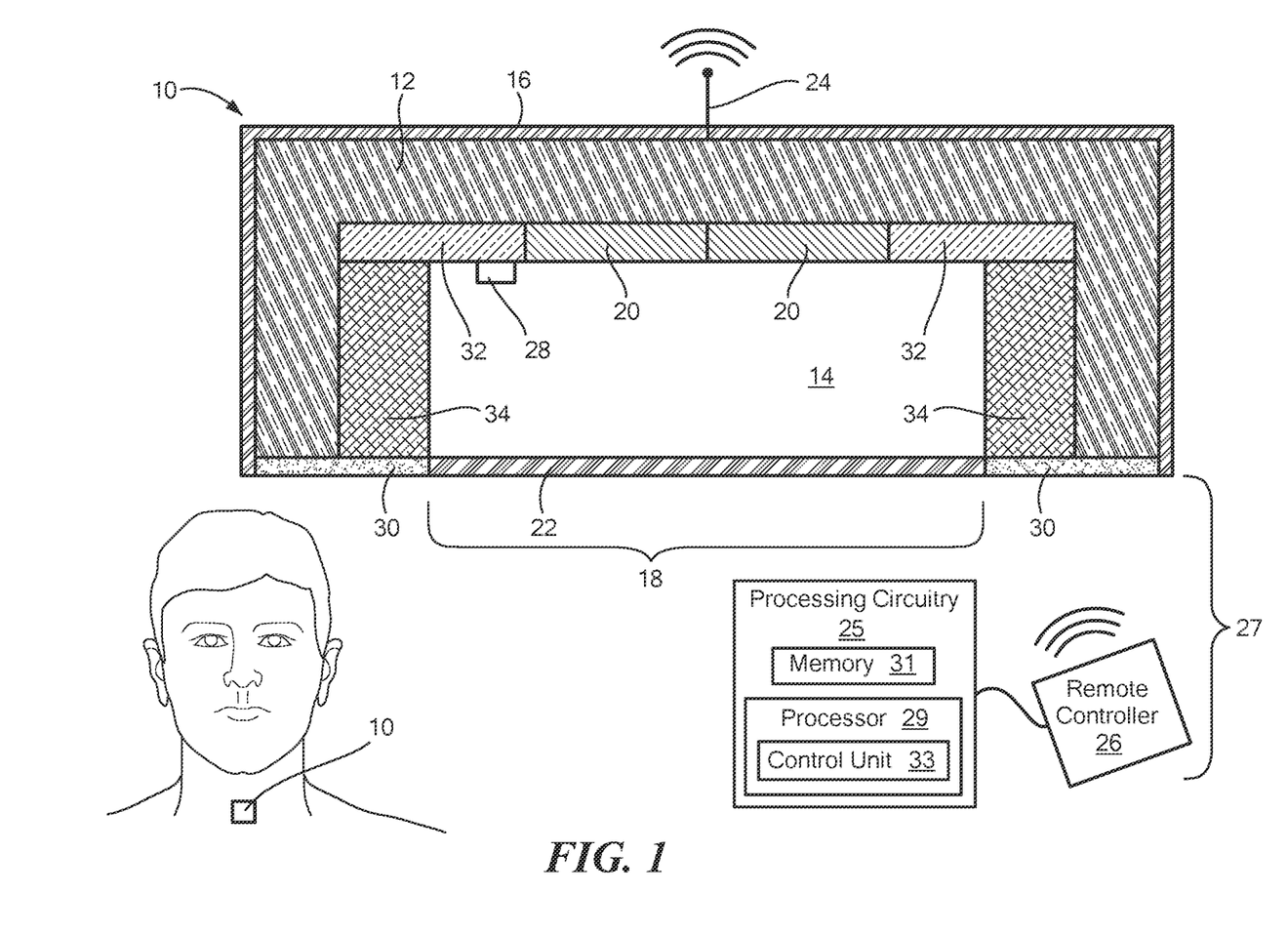
FIG. 1 is a cross-sectional view of embodiment of an acoustic sensor constructed in accordance with the principles of the present application and a view of the acoustic sensor coupled to a patient's body.
Figure 2:
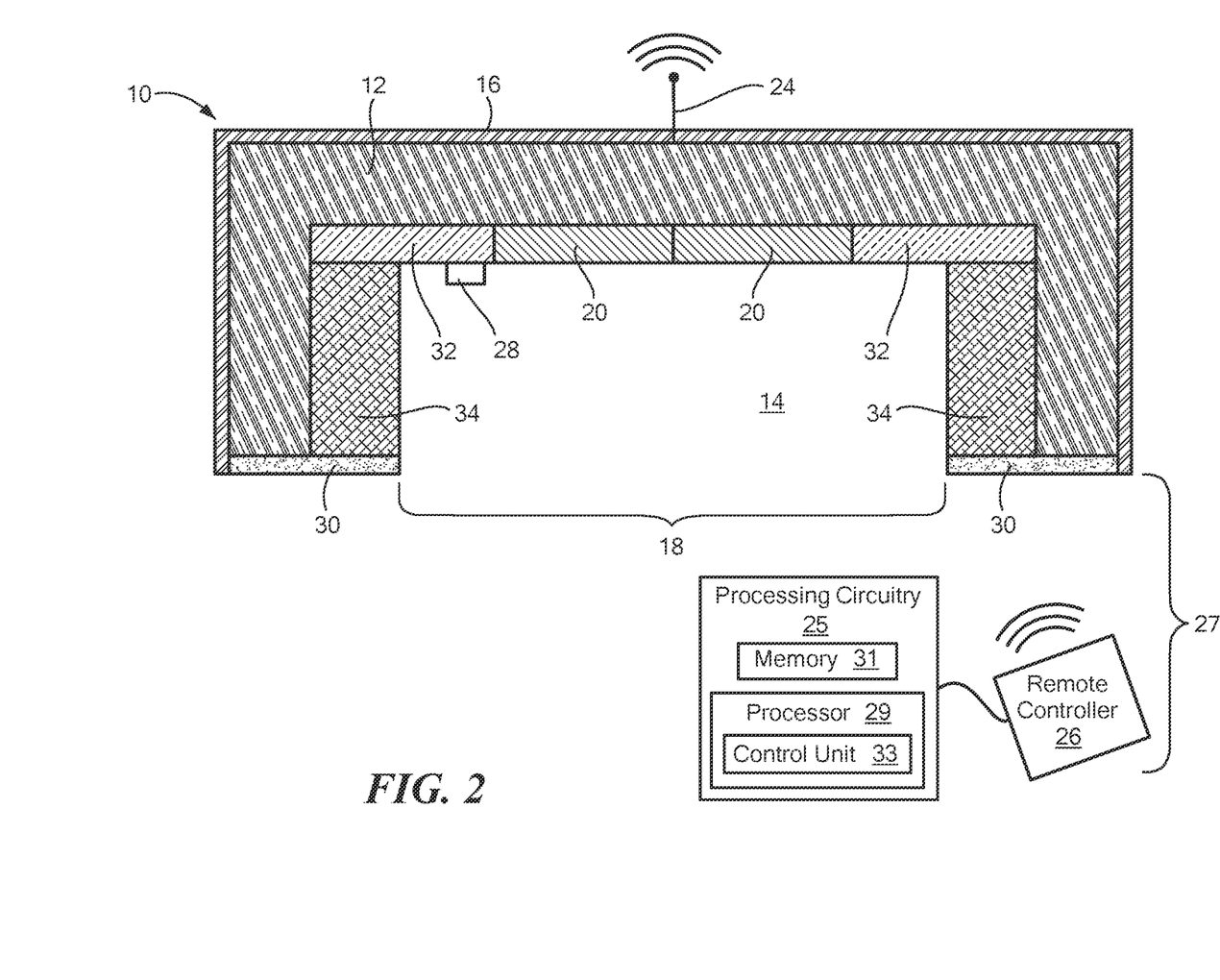
FIG. 2 is a cross-sectional view of another embodiment of an acoustic sensor constructed in accordance with the principles of the present application.
Figure 3:
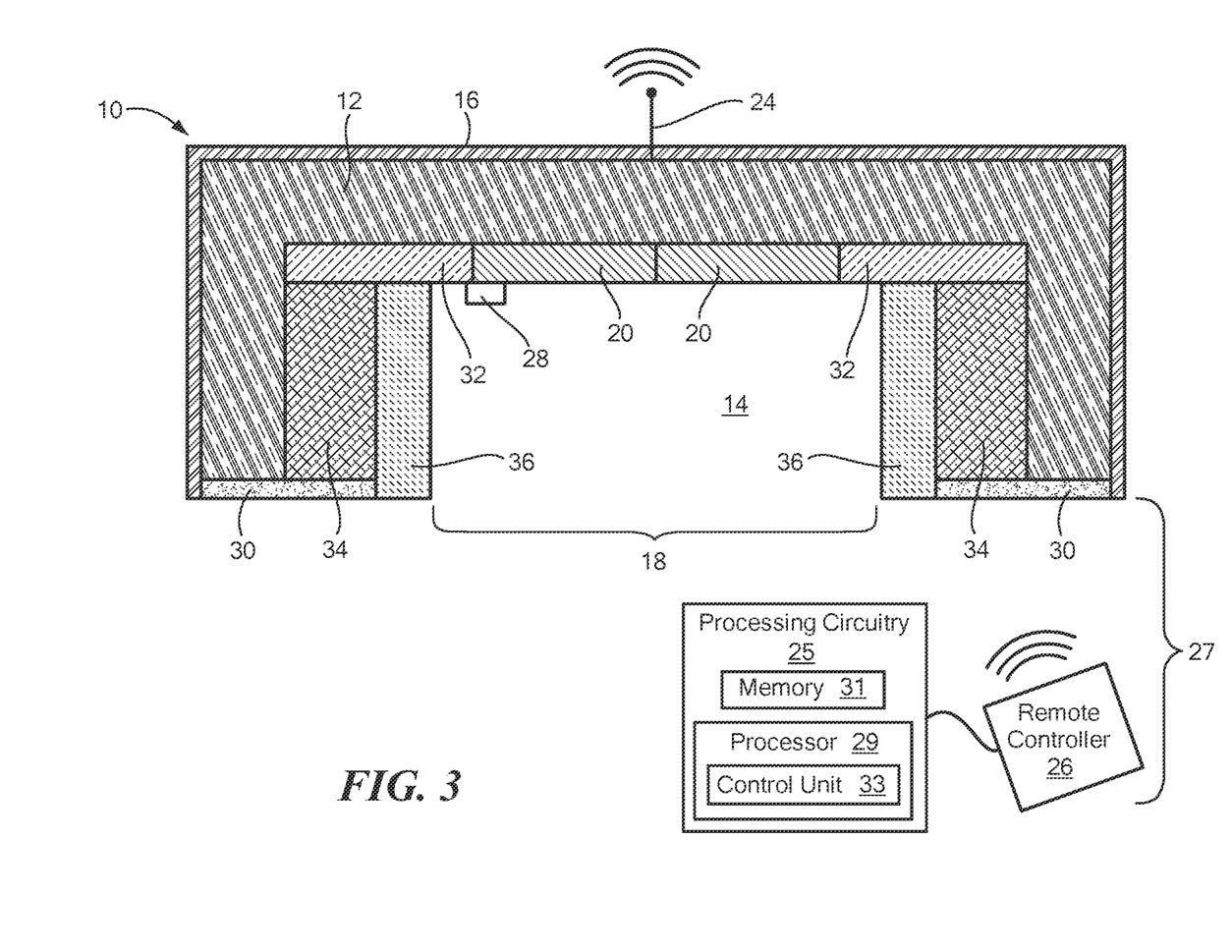
FIG. 3 is a cross-sectional view of another embodiment of an acoustic sensor constructed in accordance with the principles of the present application.
Figure 4:
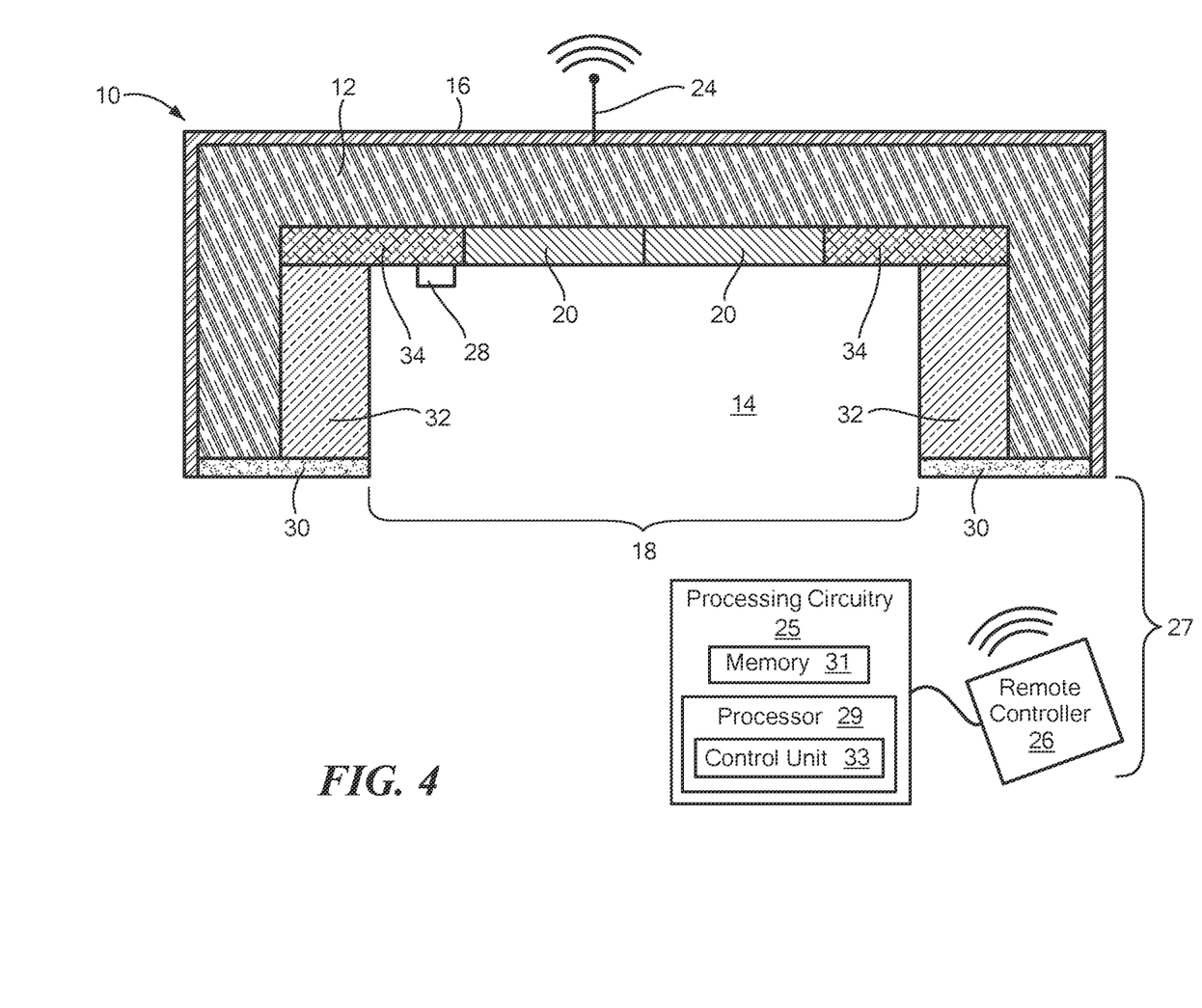
FIG. 4 is a cross-sectional view of another embodiment of an acoustic sensor constructed in accordance with the principles of the present application.
Figure 5:
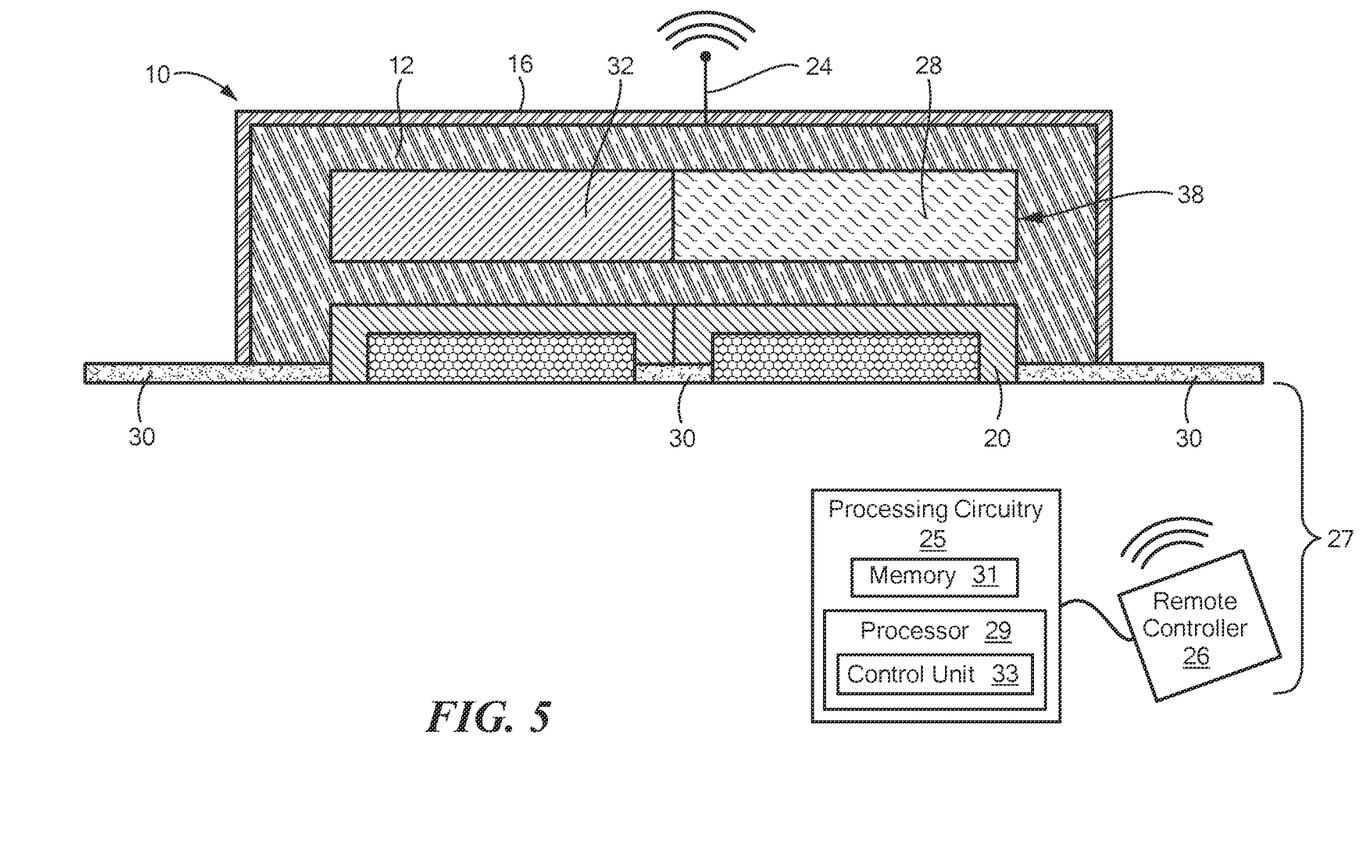
FIG. 5 is a cross-sectional view of another embodiment of an acoustic sensor constructed in accordance with the principles of the present application.
Figure 6:
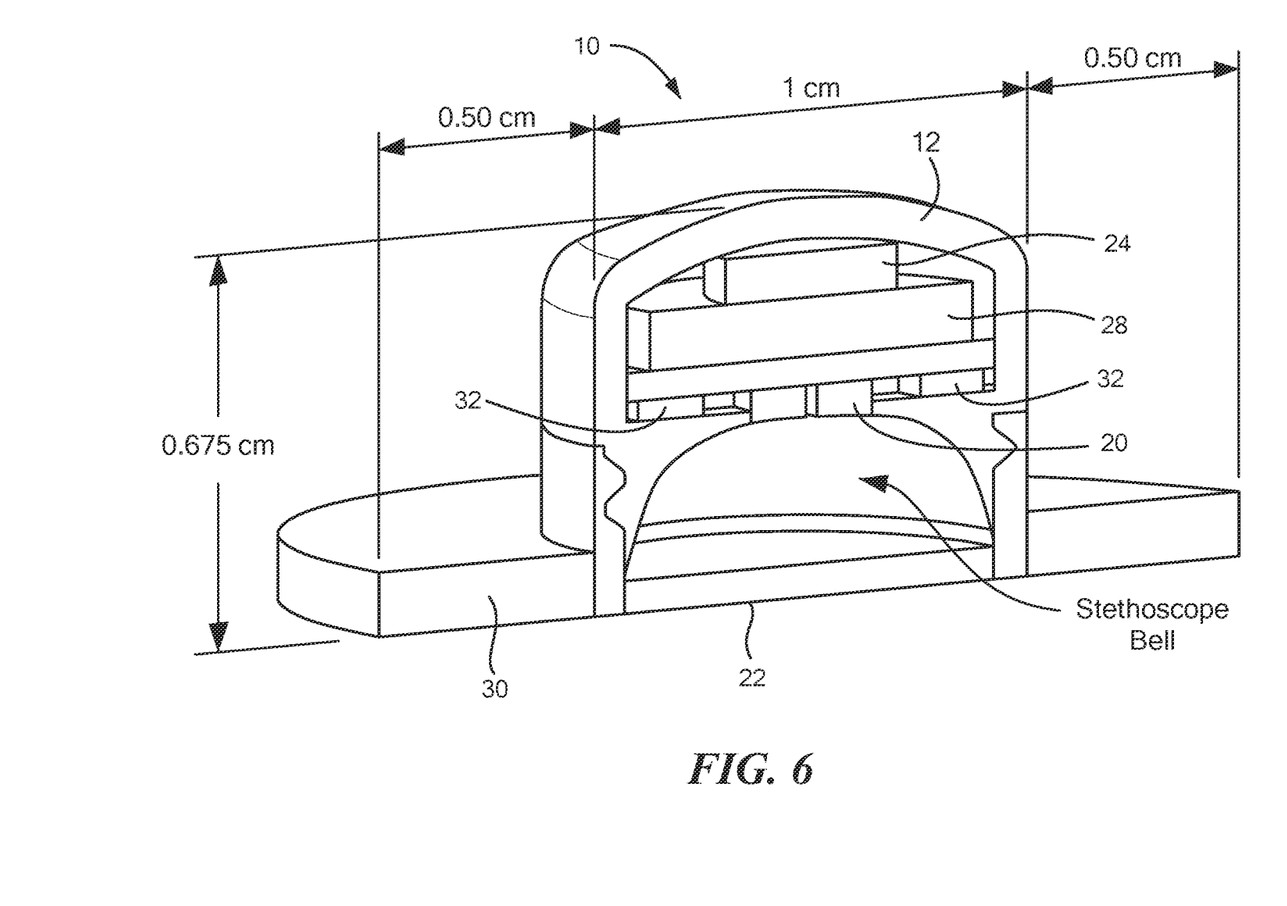
FIG. 6 is another a cross-sectional view of embodiment of an acoustic sensor constructed in accordance with the principles of the present application.

Referring now to FIG. 5, in another configuration, the sound transducer 20 may include a vibration sensor (electric, piezoelectric, or MEMS) configured to measure vibrations as a result of air flowing into and out of the trachea or lungs. The sound transducer 20 may be substantially planar with the skin of the patient to increase mechanical coupling and sensitivity. The vibration sensor accelerometer 32 and the power source 28 may be integrated into the housing 12. For example, a MEMS device may be integrated within a first chamber 38 of the housing 12 separated from the sound transducer 20. The MEMS device may further be configured to process information from one or more of the sensors disclosed herein which may be included in this configuration. The MEMS device may be included in any of the embodiments discussed above.

Figure 7:
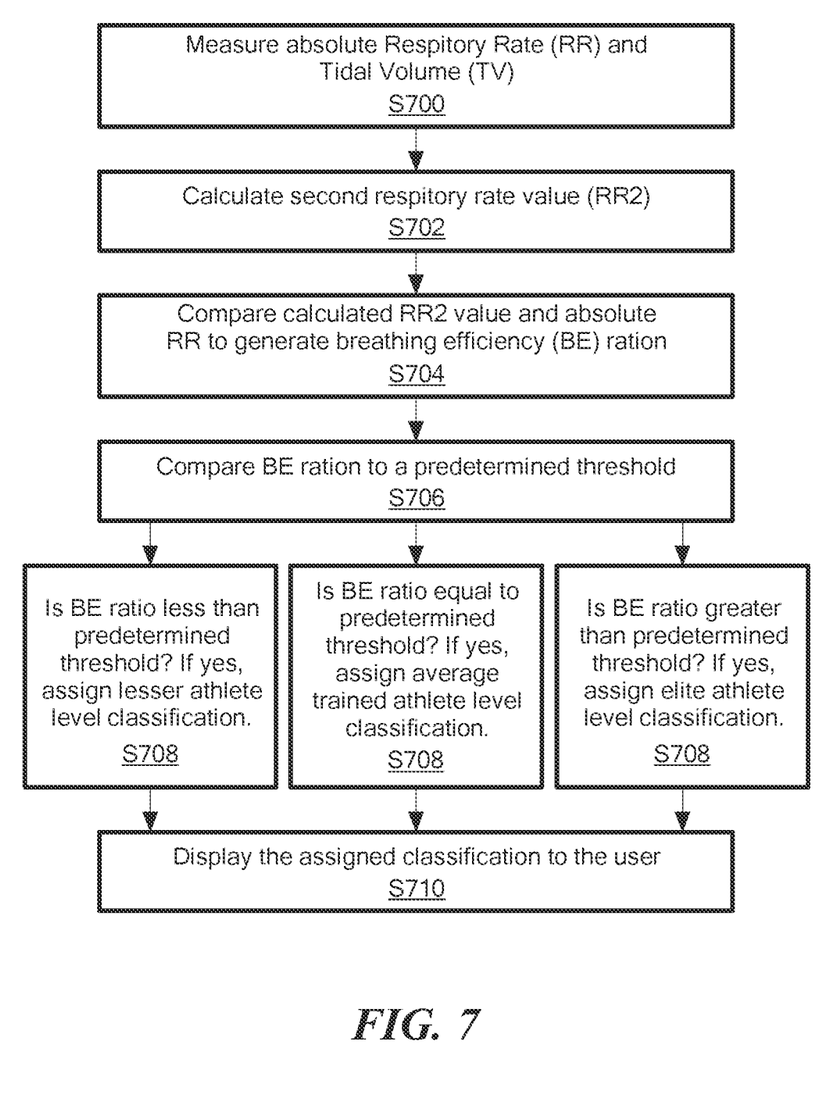
FIG. 7 is a flow chart showing exemplary steps of determining a user's respiratory function performance level before, during or after exercise, an athletic or fitness performance test, or other form of physical activity in accordance with an embodiment of the present application.

Referring now to FIG. 7, as discussed above, the controller 26 is configured to perform a method of assigning a fitness level classification to the user based on the respiratory parameters measured by the TSS 10. Primarily, the fitness level classification of the user is based on a comparison of the user's respiratory rate to a second calculated respiratory rate that is indicative of a respiratory rate of a trained athlete as similarly disclosed in Naranjo, J, et al. "A Nomogram for Assessment of Breathing Patterns during Treadmill Exercise." *British Journal of Sports Medicine*, vol. 39, no. 2, 2005, pp. 80-83., doi:10.1136/bjsm.2003.009316. This allows users wearing the TSS 10 to compare their respiratory parameters before, during, or after exercise, an athletic or fitness performance test, or any other form of physical activity, to estimated respiratory parameters of a trained athlete, and track their personal progress and improvement over time.

The method includes continuously, intermittently, and/or continually measuring the RR and TV of the user wearing the TSS 10 in real-time before, during, or after exercise, an athletic or fitness performance test, or any other form of physical activity (S700). In one embodiment, the TSS 10 and controller 26 also measure the user's heart rate, activity level, body position, body coordination, and body temperature. In one embodiment, once the user's RR and TV have been measured and transmitted to the controller 26 (e.g., the user's smart watch), a second calculated RR (RR2) value is calculated (S702) by the controller 26 and the controller 26 may use the following equations:

Men: $RR2 = 8.3465e^{0.7458(TV)}$

Women: $RR2 = 9.6446e^{0.9328(TV)}$

As shown above, "8.3465" and "9.6446" are exemplary values that are indicative of the correlation coefficients between tidal volume (TV) and breathing frequency (BF) for men and women based on the type of exercise being performed. "0.7458" and "0.9328" are exemplary values indicative of the relation between the ratio of TV to inspiratory time and ventilation, for men and women. It is to be understood that equations shown above are not limited to the specific numeric variables provided therein. Rather, the equations may include any numeric values that represent the respective correlation coefficients between TV and BF, and the relation between the ratio of TV to inspiratory time and ventilation.

Once RR2 has been calculated, the controller 26 then calculates a breathing efficiency (BE) ratio by comparing the RR2 value and the user's RR (S704). As described herein, breathing efficiency may be an indicator of the user's respiratory efficiency or respiratory fitness when compared to estimated respiratory parameters of, for example, a trained athlete. Respiratory function (how efficiency and effective a person's breathing rate and depth are in providing needed oxygen to their muscles and organs) is a key indicator of physical fitness and health. The user's BE ratio provides the user with an indication and comparison of how efficient and effective their respiratory function is when compared to an average trained athlete—someone who is capable of performing at a high level of physical activity.

Once the BE ratio has been calculated, the controller 26 then compares the ratio to a predefined threshold value or range (as shown in TABLE 1 below) to determine a classification that should be assigned to the user (S706). The threshold "1.0" is an exemplary value representative of the average breathing efficiency of a trained athlete. The threshold value is determined by calculating the average breathing efficiency before, during, or after exercise, an athletic or fitness performance test, or any other monitored form of physical activity, from a sample pool of trained professional and/or amateur athletes. If the calculated BE ratio of the user is equal to 1.0, then the user using the TSS 10 has a respiratory function performance (i.e., respiratory efficiency) substantially equivalent to the average BE of trained athletes. If the calculated BE ratio is less than 1.0, the user has a respiratory function performance which is less efficient than an average trained athlete. If the calculated BE ratio is greater than 1.0, the user has a respiratory function performance that is greater than an average trained athlete. In one configuration, based on the user's BE ratio, the controller 26 may assign the user one of the following classifications: elite athlete level (BE>1.0), trained athlete level (BE=1.0), and lesser athlete level (BE<1.0) (S708). Once the user's classification has been determined by the controller 26, the controller 26 may display the classification for the user or transmit a signal to an external display for visualization by the user (S710).

TABLE 1

Breathing Efficiency Classifications

| BE Ratio | Performance Classification |
| --- | --- |
| BE > 1.0 | Elite Athlete Level |
| BE = 1.0 | Average Trained Athlete Level |
| BE < 1.0 | Lesser Athlete Level |

It will be understood that as described herein, the present embodiments are not limited to the aforementioned classification terminology. Rather, in alternative embodiments, the controller 26 may assign any classification that is indicative of the user's respiratory efficiency level when compared to estimated respiratory parameters of an average trained athlete. The controller 26 is not limited to assigning only an elite athlete level, a trained athlete level, or a lesser athlete level to the user.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate, and that modifications and variations are possible of achieving the electrical and data communication.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

The invention claimed is:

1. A method of determining a fitness level of a user comprising:
    wirelessly receiving at a controller, from a physiological sensor to be positioned on the user proximate the user's chest, throat, or mouth, configured to measure an airflow, an airflow value being based on a measurement of the airflow of the user using the physiological sensor;
    correlating the measured airflow value into a measurement of the user's respiratory rate and tidal volume;
    calculating a respiratory rate value by inputting the measured tidal volume into an exponential regression equation and relating the respiratory rate and the tidal volume to calculate the respiratory rate value;
    calculating a breathing efficiency (BE) ratio based on a comparison of the user's measured respiratory rate and the calculated respiratory rate value;
    correlating the calculated BE ratio to a predetermined threshold; and
    assigning a classification to the user based on the calculated BE ratio, the classification being indicative of the user's respiratory function performance.

2. The method of claim 1, wherein the assigned classification is one selected from the group consisting of:
    an elite athlete level;
    a trained athlete level; and
    a lesser athlete level.

3. The method of claim 2, wherein:
    the elite athlete level classification is assigned when the BE ratio is greater than the predetermined threshold;
    the trained athlete level classification is assigned when the BE ratio is equal to the predetermined threshold; and
    the lesser athlete level classification is assigned when the BE ratio is less than the predetermined threshold.

4. The method of claim 3, wherein the elite athlete level has a BE>1.0, the trained athlete level has a BE=1.0, and the lesser athlete level has a BE<1.0.

5. The method of claim 1, wherein the respiratory rate value is calculated using the measured tidal volume with a first equation for men and a second equation for women, the first equation being $RR2=8.3465e^{0.7458(tidal\ volume)}$ and the second equation being $RR2=9.6446e^{0.9328(tidal\ volume)}$.

* * * * *